United States Patent
Kato et al.

[11] Patent Number: 5,945,121
[45] Date of Patent: Aug. 31, 1999

[54] LIPOSOME EYE DROPS

[75] Inventors: Muneyoshi Kato; Tomohiro Ohtsuki; Fuminobu Egami; Kenji Tsunoda, all of Tokyo, Japan

[73] Assignee: Taisho Pharmaceutical Co., Ltd., Tokyo, Japan

[21] Appl. No.: 08/836,740

[22] PCT Filed: Dec. 19, 1995

[86] PCT No.: PCT/JP95/02599

§ 371 Date: May 15, 1997

§ 102(e) Date: May 15, 1997

[87] PCT Pub. No.: WO96/19211

PCT Pub. Date: Jun. 27, 1996

[30] Foreign Application Priority Data

Dec. 19, 1994 [JP] Japan .................................. 6-314437

[51] Int. Cl.⁶ .................................................. A61K 9/127
[52] U.S. Cl. ........................................ 424/450; 424/427
[58] Field of Search .................................. 424/450, 427

[56] References Cited

U.S. PATENT DOCUMENTS

| | | | |
|---|---|---|---|
| 4,818,537 | 4/1989 | Guo | 424/427 |
| 5,389,383 | 2/1995 | Huth | 424/450 |
| 5,565,213 | 10/1996 | Nakamari | 426/450 |

FOREIGN PATENT DOCUMENTS

| | | | |
|---|---|---|---|
| 1548892 | 11/1993 | Australia . | |
| 0 623 314 A1 | 6/1994 | European Pat. Off. | A61K 31/70 |
| 64-42424 | 2/1989 | Japan | A61K 31/185 |
| 0 409 999 | 1/1990 | Japan | A61K 31/665 |
| 2-501730 | 6/1990 | Japan | A61K 9/127 |
| 7-48262 | 2/1995 | Japan | A61K 31/70 |
| WO 90/08548 | 1/1990 | WIPO | A61K 31/665 |
| WO 94 11100 | 5/1994 | WIPO . | |

OTHER PUBLICATIONS

International Search Report.

*Primary Examiner*—Gollamudi S. Kishore
*Attorney, Agent, or Firm*—Sughrue, Mion, Zinn, Macpeak & Seas, PLLC

[57] ABSTRACT

Liposome eye drops contain taurine, glucose and inorganic salts having a pH of 5.5–8.0. The osmolarity is between 250 and 450 mOsm and at least a portion of the taurine and inorganic salts is encapsulated in the liposomes. A preferred embodiment also contains aspartate.

2 Claims, 1 Drawing Sheet

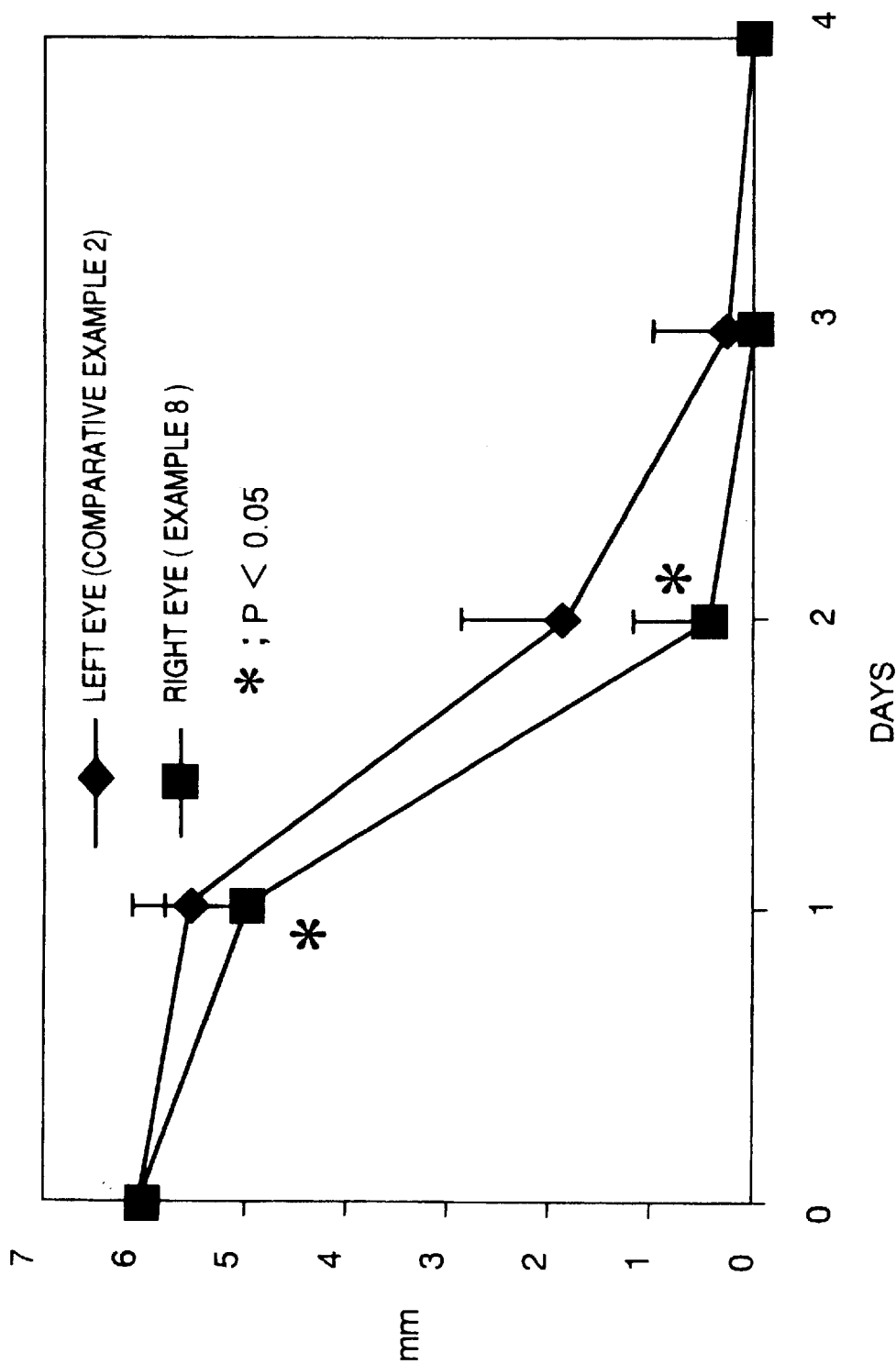

LIPOSOME EYE DROPS

This application is a 371 of PCT/JP95/02599 filed Dec. 19, 1995.

TECHNICAL FIELD

The present invention relates to liposome eye drops useful for treating dry eye or mitigating its symptoms.

BACKGROUND ART

Dry eye (dried state of eyes, reduction of tear fluid) causes discomfort (e.g. dry feeling, hot feeling, eye strain, etc.), corneal injury, corneal damage and the like. In the past, dry eye has been treated by using artificial tear fluids containing boric acid, sodium chloride, potassium chloride, calcium chloride and the like. In addition, there is a proposal for the use of a liposome composition containing a quaternary benzylamine (Japanese Patent Kohyo 2-501730).

However, such prior art has an insufficient effect on mitigating or treating symptoms caused by dry eye.

An object of the present invention is to provide eye drops which have excellent mitigating or treating effects on symptoms caused by dry eye.

DISCLOSURE OF THE INVENTION

As a result of extensive research, the present inventors have found that eye drops comprising a specific composition can achieve the above-problems, and whereby the present invention has been accomplished.

That is, the present invention relates to liposome eye drops comprising taurine, glucose and inorganic salts.

In the present invention, the inorganic salts mean a mixture containing sodium chloride and potassium chloride, and if desired, one or two members selected from the group consisting of calcium chloride, magnesium sulfate and sodium bicarbonate.

The amount of taurine is preferably from 0.5 to 3% by weight. In case where the amount of taurine is less than 0.5% by weight, the treating effect on dry eye is weak, and in case where it is more than 3% by weight, irritation to eye occurs due to hypertonia. The amount of glucose is preferably from 0.01 to 1% by weight, more preferably from 0.03 to 0.2% by weight. In case where the amount of glucose is less than 0.01% by weight, the treating effect on dry eye is weak, and in case where it is more than 1% by weight, the eye drops give discomfort to eye when applied.

In order to enhance the effect of the present invention, the components are preferably combined in such an amount rate that the liposome eye drops prepared finally show a pH of 5.5 to 8.0 and an osmotic pressure of 250 to 450 mOsm. Furthermore, the liposome eye drops contain preferably an aspartate (e.g. magnesium L-aspartate, potassium L-aspartate, magnesium potassium L-aspartate, etc.) as a component. In this case, the amount of the aspartate is preferably 0.01 to 0.5% by weight, and more preferably 0.03 to 0.2% by weight.

A lecithin for composing liposome may be contained in such an amount that the eye drops have an enhanced retentivity on the corneal surface when applied, and that the eye drops do not aggregate when stored, and are stable in galenical pharmacy. That is, the amount of the lecithin is preferably 0.03 to 0.8% by weight, and more preferably 0.05 to 0.5% by weight.

The liposome eye drops of the present invention can be easily prepared by using an ordinary method used for the preparation of a liposome aqueous suspension, for example, a method described in Japanese Patent Kokai 5-4037 or a method described in Japanese Patent Kokai 2-167218 which comprises dispersing an easily hydrolyzable lecithin with other components in water and sizing.

According to the present invention, besides the above-mentioned essential components, if desired, it is possible to contain further components or other active ingredients usable for the preparation of ordinary eye drops, as long as the effects of the present invention are not degraded, for example, neostigmine methyl sulfate, anti-inflammatory agents (e.g. dipotassium glycyrrhizinate, $\epsilon$-aminocaproic acid, allantoin, berberine chloride, berberine sulfate, sodium azulene sulfonate, zinc sulfate, zinc lactate, lysozyme chloride, etc.), antihistaminic agents (e.g. diphenhydramine hydrochloride, chlorpheniramine maleate, etc.), hyperemia-releasing agents (e.g. naphazoline hydrochloride, tetrahydrozoline hydrochloride, phenylephrine hydrochloride, etc.), vitamins [e.g. an activated vitamin $B_2$ (flavin adenine dinucleotide sodium), vitamin $B_6$ (pyridoxine hydrochloride), vitamin $B_{12}$ (cyanocobalamin), vitamin A acetate (retinol acetate), vitamin E acetate (tocopherol acetate), panthenol, calcium pantothenate, sodium pantothenate, etc.], amino acids (e.g. magnesium potassium L-aspartate, potassium L-aspartate, magnesium L-aspartate, sodium chondroitin sulfate, etc.), refrigerants (e.g. menthol, borneol, camphor, mentha oil, etc.), polymer additives (e.g. a polyhydric alcohol, polyvinyl alcohol, polyvinylpyrrolidone, methyl cellulose, hydroxyethyl cellulose, hydroxypropylmethyl cellulose, etc.), stabilizers (e.g. ethylenediamine tetraacetate, etc.), preservatives (e.g. benzalkonium chloride, methyl paraben, sorbic acid, etc.), sulfa drugs and the like.

INDUSTRIAL UTILIZABILITY

The present invention makes it possible to provide eye drops having an enhanced retentivity on corneal surface, and an excellent effect for repairing corneal injury and corneal damage. Accordingly, the liposome eye drops of the present invention are useful for mitigating and treating symptoms caused by dry eye.

BRIEF DESCRIPTION OF THE DRAWING

FIG. 1 is a graph showing the repairing degree of the injured cornea wherein the vertical line is the width (mm) of the unrepaired cornea and the horizontal line is days.

BEST MODE FOR CARRYING OUT THE INVENTION

The present invention is illustrated in more detail by the following examples and test examples.

EXAMPLE 1

1000 mg of taurine, 100 mg of glucose, 100 mg of an easily hydrolyzable hydrogenated soybean lecithin, 40 mg of sodium chloride, 10 mg of potassium chloride and 3000 mg of mannitol were dispersed and emulsified in 95 ml of sterile purified water by using a homogenizer. The resulting suspension was subjected to sizing according to a polycarbonate filter method, and adjusted to pH 7.4 with sodium hydroxide. Sterile purified water was added to the suspension up to a total volume of 100 ml, whereby there were obtained liposome eye drops whose osmotic pressure was 286 mOsm as a result of the measurement.

EXAMPLE 2

Following the same procedure as in Example 1 except for using 3000 mg of taurine in place of 1000 mg of taurine, 125 mg of an easily hydrolyzable hydrogenated soybean lecithin in place of 100 mg of an easily hydrolyzable hydrogenated soybean lecithin and 860 mg of mannitol in place of 3000 mg of mannitol, and adjusting to pH 8.0 with sodium hydroxide, whereby there were obtained liposome eye drops whose osmotic pressure was 330 mOsm as a result of the measurement.

EXAMPLE 3

Following the same procedure as in Example 1 except for using 500 mg of taurine in place of 1000 mg of taurine and 150 mg of an easily hydrolyzable hydrogenated soybean lecithin in place of 100 mg of an easily hydrolyzable hydrogenated soybean lecithin, and adjusting to pH 6.0 with sodium hydroxide, whereby there were obtained liposome eye drops whose osmotic pressure was 255 mOsm as a result of the measurement.

EXAMPLE 4

Following the same procedure as in Example 1 except for using 30 mg of sodium chloride in place of 40 mg of sodium chloride and 2900 mg of mannitol in place of 3000 mg of mannitol, and further using 50 mg of sodium bicarbonate, whereby there were obtained liposome eye drops whose osmotic pressure was 286 mOsm as a result of the measurement.

EXAMPLE 5

Following the same procedure as in Example 1 except for using 30 mg of sodium chloride in place of 40 mg of sodium chloride and 2900 mg of mannitol in place of 3000 mg of mannitol, and further using 100 mg of magnesium potassium aspartate, whereby there were obtained liposome eye drops whose osmotic pressure was 286 mOsm as a result of the measurement.

EXAMPLE 6

Following the same procedure as in Example 1 except for using 30 mg of sodium chloride in place of 40 mg of sodium chloride and 2950 mg of mannitol in place of 3000 mg of mannitol, and further using 40 mg of magnesium potassium aspartate, 10 mg of sodium bicarbonate and 10 mg of sodium borate, whereby there were obtained liposome eye drops whose osmotic pressure was 286 mOsm as a result of the measurement.

EXAMPLE 7

To a solution of 1000 mg of taurine, 100 mg of glucose, 23 mg of sodium chloride, 8 mg of potassium chloride, 3000 mg of mannitol and [$^3$H] inulin (0.25 mCi) in 90 ml of sterile purified water was added 125 mg of an easily hydrolyzable hydrogenated soybean lecithin for composing liposome, and the mixture was dispersed and emulsified by using a homogenizer. The resulting suspension was subjected to sizing according to a polycarbonate filter method, adjusted to pH 7.4 with sodium hydroxide, and made up to a total volume of 100 ml by adding sterile purified water, whereby there were obtained liposome eye drops whose osmotic pressure was 286 mOsm as a result of the measurement.

EXAMPLE 8

To a solution of 1000 mg of taurine, 100 mg of glucose, 23 mg of sodium chloride, 8 mg of potassium chloride and 3000 mg of mannitol in 90 ml of sterile purified water was added 125 mg of an easily hydrolyzable hydrogenated soybean lecithin for composing liposome, and the mixture was dispersed and emulsified by using a homogenizer. The resulting suspension was subjected to sizing according to a polycarbonate filter method, adjusted to pH 7.4 with sodium hydroxide, and made up to a total volume of 100 ml by adding sterile purified water, whereby there were obtained liposome eye drops whose osmotic pressure was 286 mOsm as a result of the measurement.

COMPARATIVE EXAMPLE 1

A solution of 750 mg of sodium chloride, 90 mg of potassium chloride and [$^3$H] inulin (0.25 mCi) in 90 ml of sterile purified water was adjusted to pH 7.4 with sodium hydroxide, and made up to a total volume of 100 ml by adding sterile purified water, whereby there were obtained artificial tear fluid type eye drops whose osmotic pressure was 286 mOsm as a result of the measurement.

COMPARATIVE EXAMPLE 2

A solution of 1000 mg of taurine, 23 mg of sodium chloride, 8 mg of potassium chloride and 3000 mg of mannitol in 90 ml of sterile purified water was adjusted to pH 7.4 with sodium hydroxide, and made up to a total volume of 100 ml by adding sterile purified water, whereby there were obtained eye drops whose osmotic pressure was 286 mOsm as a result of the measurement.

TEST EXAMPLE 1

Four to six male Japanese albino rabbits, 12–16 weeks-old, weighing 3.2–4.2 kg were used for each group. After confirmation of no abnormality in the eye before testing, 250 μl of the eye drops obtained in Example 7 was topically applied to the right eye, and 250 μl of the eye drops obtained in Comparative Example 1 was topically applied to the left eye. Five minutes, 15 minutes or 30 minutes after the topical application, the corneas were collected, and the radioactivity retained on the cornea was measured. As a result, the retention on the cornea of the eye drops obtained in Example 7 was significantly greater than that of eye drops obtained in Comparative Example 1 (Table 1).

TABLE 1

| | Radioactivity on cornea of eye drops (CPM) | |
|---|---|---|
| | Example 7 | Comparative Example 1 |
| after 5 min. | 916.5* | 28.5 |
| after 15 min. | 334.7** | 8.2 |
| after 30 min. | 121.2** | 11.7 |

*$p < 0.05$
**$p < 0.01$

TEST EXAMPLE 2

Seven male Japanese albino rabbits, 10–12 weeks-old, weighing 3.0–3.2 kg were used. After confirmation of no abnormality in the eye before testing, an absorption paper (6.0 mm in diameter) soaked in n-heptanol was placed on the center of the cornea of both eyes for one minute, and the corneal epithelium was removed. 100 μl of the eye drops obtained in Example 8 was applied to the right eye immediately after the removal, and repeatedly applied 4 times per day for 5 days, and 100 μl of the eye drops obtained in Comparative Example 2 was similarly applied to the left eye. The unrepaired site of the corneal epithelium was dyed with a 1% methylene-blue solution, and the width (the longest) of the unrepaired site was measured for evaluation.

As a result, the eye drops obtained in Example 8 showed faster repairing effect than the eye drops obtained in Comparative Example 2 (FIG. 1).

We claim:

1. Liposome eye drops comprising 0.5 to 3% by weight of taurine, 0.01 to 1% by weight of glucose, and inorganic salts, and having a pH of 5.5 to 8.0 and an osmotic pressure of 250 to 450 mOsm, wherein at least a portion of said glucose, said taurine and said inorganic salts is encapsulated in a liposome of said liposome eye drops.

2. Liposome eye drops comprising 0.5 to 3% by weight of taurine, 0.01 to 1% by weight of glucose, and inorganic salts, and having a pH of 5.5 to 8.0 and an osmotic pressure of 250 to 450 mOsm, and 0.01 to 0.5% by weight of an aspartate, wherein at least a portion of said glucose, said taurine and said inorganic salts being is encapsulated in a liposome of said liposome eye drops.

* * * * *